(12) United States Patent
Briggs et al.

(10) Patent No.: US 10,045,096 B2
(45) Date of Patent: Aug. 7, 2018

(54) SOCIAL MEDIA MODIFICATION OF BEHAVIOR AND MOBILE SCREENING FOR IMPAIRMENT

(71) Applicant: International Business Machines Corporation, Armonk, NY (US)

(72) Inventors: Benjamin D. Briggs, Waterford, NY (US); Lawrence A. Clevenger, LaGrangeville, NY (US); Leigh Anne H. Clevenger, Rhinebeck, NY (US); Jonathan H. Connell, II, Cortlandt Manor, NY (US); Nalini K. Ratha, White Plains, NY (US); Michael Rizzolo, Albany, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/934,992

(22) Filed: Nov. 6, 2015

(65) Prior Publication Data
US 2017/0134832 A1    May 11, 2017

(51) Int. Cl.
*H04Q 9/00* (2006.01)
*A61B 5/00* (2006.01)

(52) U.S. Cl.
CPC .............. *H04Q 9/00* (2013.01); *A61B 5/00* (2013.01); *H04Q 2209/40* (2013.01); *H04Q 2209/823* (2013.01)

(58) Field of Classification Search
CPC .............. H04Q 9/00; H04Q 2209/40; H04Q 2209/823; G06F 19/322; G06F 19/3418; G06Q 10/10; G06Q 50/24; A61B 5/00; A61B 5/002; G08B 21/0407; G08B 21/0415; G08B 21/0423; G08B 21/043; G08B 21/0438; G08B 21/0446;
(Continued)

(56) References Cited

U.S. PATENT DOCUMENTS 6,886,653 B1    5/2005    Bellehumeur
6,967,581 B2   11/2005    Karsten
(Continued)

OTHER PUBLICATIONS

M. Swan, "Sensor mania! the internet of things, wearable computing, objective metrics, and the quantified self 2.0," Journal of Sensor and Actuator Networks, vol. 1, No. 3, Nov. 2012, pp. 217-253.
(Continued)

*Primary Examiner* — Brian Wilson
(74) *Attorney, Agent, or Firm* — Vazken Alexanian; Michael J. Chang, LLC

(57) ABSTRACT

Techniques for modifying user behavior and screening for impairment using a mobile feedback controller, such as a smartwatch, are provided. In one aspect, a method for monitoring a user includes the steps of: collecting real-time data from the user, wherein the data is collected via a mobile feedback controller worn by the user; determining whether the data collected from the user indicates impairment; determining appropriate corrective actions to be taken if the data collected from the user indicates impairment, otherwise continuing to collect data from the user in real-time; determining whether any action is needed; and undertaking the appropriate corrective actions if action is needed, otherwise continuing to collect data from the user in real-time.

20 Claims, 3 Drawing Sheets

(58) Field of Classification Search
CPC .... G08B 21/0453; G08B 21/06; G08B 23/00; G08B 25/00; G08B 21/02
USPC ...... 340/870.01, 500, 539.1, 539.12, 539.22, 340/540, 573.1, 575, 576, 573.7, 10.1
See application file for complete search history.

(56) References Cited

U.S. PATENT DOCUMENTS

| | | |
|---|---|---|
| 7,911,350 B2 | 3/2011 | Shoji et al. |
| 8,606,592 B2 | 12/2013 | Hyde et al. |
| 9,019,107 B2 | 4/2015 | Biondo et al. |
| 9,028,405 B2 | 5/2015 | Tran |
| 2009/0325639 A1* | 12/2009 | Koehn ................. B60K 28/063 455/556.1 |
| 2013/0093603 A1* | 4/2013 | Tschirhart ................ A61B 5/18 340/902 |
| 2014/0052567 A1* | 2/2014 | Bhardwaj .......... G06Q 30/0631 705/26.7 |
| 2014/0081179 A1 | 3/2014 | Moore-Ede |
| 2014/0125491 A1* | 5/2014 | Park ...................... H04W 4/027 340/870.01 |
| 2014/0306826 A1* | 10/2014 | Ricci .................... H04W 48/04 340/573.1 |
| 2015/0182160 A1 | 7/2015 | Kim et al. |

OTHER PUBLICATIONS

J. Bartlett, "Nissan Nismo smart watch puts car performance data on your wrist," ConsumerReports.org, Published: Sep. 9, 2013, 1 page.
BACtrack, "BACtrack® Announces App for Apple Watch; Provides First-Ever Continuous Estimate of BAC (Blood Alcohol Content) via Glances Feature," PRNewswire, Apr. 8, 2015, 3 pages.

* cited by examiner

SOCIAL MEDIA MODIFICATION OF BEHAVIOR AND MOBILE SCREENING FOR IMPAIRMENT

FIELD OF THE INVENTION

The present invention relates to user behavior, and more particularly, to modification of user behavior and screening for impairment using a mobile feedback controller, such as a smartwatch.

BACKGROUND OF THE INVENTION

Impairment, whether it be from a medical condition, fatigue, medication, etc., can pose risks especially in situations where individuals need to be alert, such as when walking, driving, or performing other activities. Existing techniques for assessing a person's condition tend to focus on single point in time readings taken at fixed locations. However, the conditions affecting a person's abilities can change dynamically. For instance, a person suffering a medical condition might become increasingly more impaired over time. It would be useful to be able to monitor this condition over time, and solicit assistance if necessary. One could not, however, accomplish this using existing technology.

Current mobile devices (which are oftentimes kept on one's person throughout the day) offer a wide range of sensing and user-interactive technology. For instance, smartwatches are becoming a popular accessory for individuals to wear on a daily basis. Unlike conventional watches, a smartwatch has the capabilities to gather and disseminate information. For instance, instead of simply giving the user the time, smartwatches can collect data from the user, from the environment, from the Internet, etc. Smartwatches can also interact with the user, for example, alerting the user when certain conditions such as increased heart rate occur during exercise.

Therefore, techniques which leverage emerging smart mobile technology to screen and/or modify a person's conditions and/or behavior thereby avoiding dangerous situations would be desirable.

SUMMARY OF THE INVENTION

The present invention provides techniques for modifying user behavior and screening for impairment using a mobile feedback controller. In one aspect of the invention, a method for monitoring a user is provided. The method includes the steps of: collecting real-time data from the user, wherein the data is collected via a mobile feedback controller worn by the user; determining whether the data collected from the user indicates impairment; determining appropriate corrective actions to be taken if the data collected from the user indicates impairment, otherwise continuing to collect data from the user in real-time; determining whether any action is needed; and undertaking the appropriate corrective actions if action is needed, otherwise continuing to collect data from the user in real-time.

A more complete understanding of the present invention, as well as further features and advantages of the present invention, will be obtained by reference to the following detailed description and drawings.

DETAILED DESCRIPTION OF PREFERRED EMBODIMENTS

As provided above, current smart mobile technology offers a wide variety of capabilities for information gathering and interaction with a user. Advantageously, provided herein are techniques for leveraging those capabilities to monitor an individual's condition and/or to modify the individual's behavior through either interacting with the individual (or others) to avoid dangerous situations from occurring. Take for instance the situation where a person is out and needs to drive herself home. The person is however suffering an impairment due, for example, to a medical condition (e.g., dizziness as a result of high blood pressure), fatigue (e.g., due to sleep condition), etc. The present techniques can be used to assess the user's condition based, for example, on the user's behavior, determine whether an impairment situation exists (for instance to screen whether the behavior is caused by a medical condition resulting in unconsciousness, or simply that the user is asleep at home), and what actions if any should be taken (for instance alerting medical personnel in the case of a medical emergency, prevent the user's automobile from turning on thus preventing the user from driving, arranging for alternative transportation such as a taxi, etc.). The present techniques utilize this intelligent technology to determine whether action is needed. For instance, if it is detected that the user is experiencing drowsiness (e.g., low heart rate, sluggish movements, etc.) but it is determined that the user is already at home, then action might not be necessary. On the other hand, if the user is found to be away from home and needing to drive, then the users and/or others may be alerted to this condition.

Figure 1:
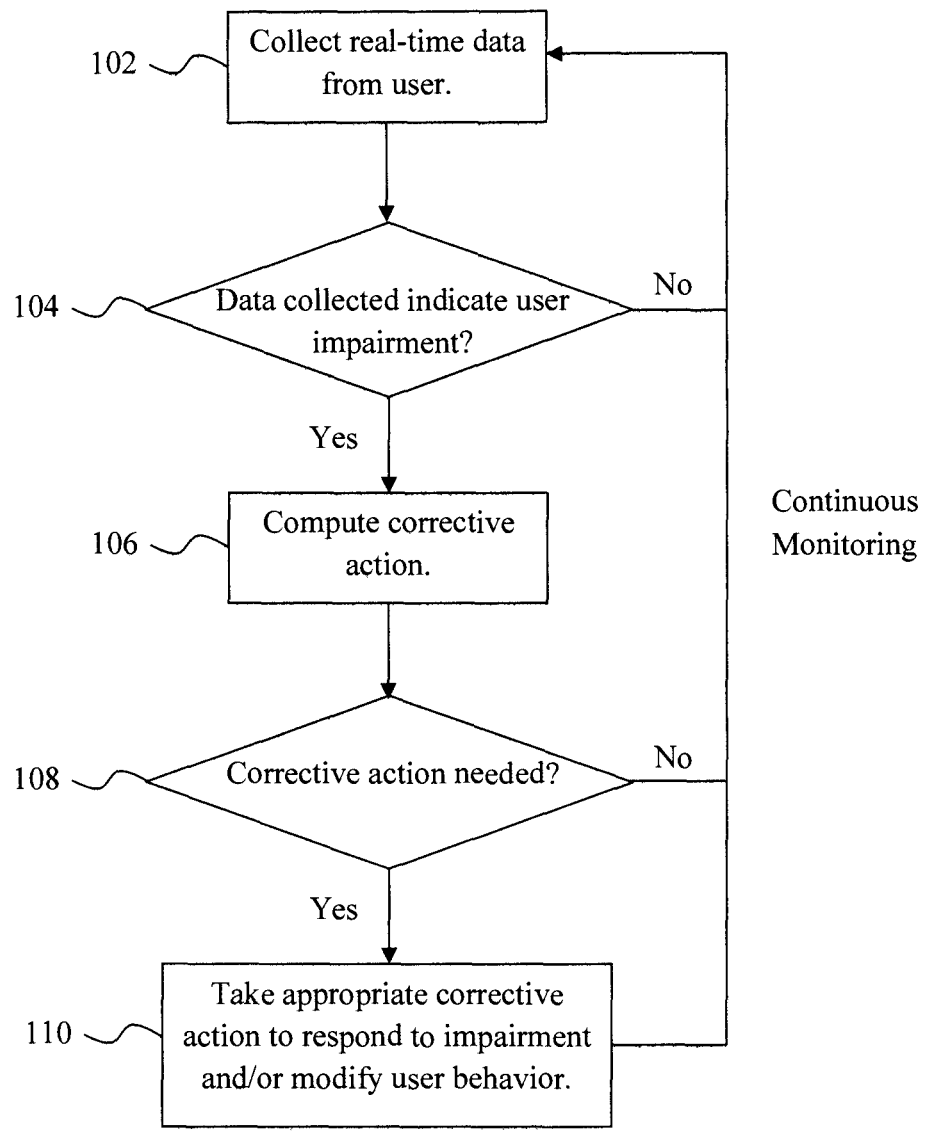
FIG. 1 is a diagram illustrating an exemplary methodology for user behavior monitoring and feedback control using a wearable controller such as a smartwatch according to an embodiment of the present invention.

An overview of the present techniques is now provided by way of reference to methodology 100 of FIG. 1. In step 102, real-time data is gathered from the user and/or from the user's surroundings. As highlighted above, according to an exemplary embodiment, the present techniques for behavior monitoring and feedback control are implemented using wearable mobile technology, such as a commercially available smartwatch. A smartwatch, or other suitable wearable technology, may also be referred to herein as a wearable mobile feedback controller or simply a wearable controller. Smartwatches which may be used in accordance with the present techniques are available from companies such as Motorola™ (e.g., the MOTO 360), Samsung™ (e.g., Samsung Gear™), Apple™ (e.g., the Apple Watch™), etc.

Different smartwatches have different capabilities, such as a variety of different sensors, user interactive features such as voice commands, audible/motion alarms/alerts, etc. By way of example only, some of the smartwatch technology that is leveraged for the present techniques includes the following:

Sensors—the present techniques envision use of one or more sensors proximate to the user (also referred to herein as proximal sensors). These are sensors that can measure physical/physiological conditions of the user. These types of sensors generally require contact with the user to function, and thus are also referred to herein as contact sensors. For instance, one such contact sensor is an electrodermal activity or EDA sensor. EDA sensors measure the electrical characteristics of the skin. The electrical characteristics of the skin are controlled, at least in part, by the state of sweat glands in the skin, which in turn are regulated by the sympathetic nervous system. Thus, EDA sensors can gauge sympathetic and nervous responses.

Other contact sensors useful for the present techniques include pulse oximeters and heart rate sensors. A pulse oximeter measures a person's blood oxygen levels often via a sensor placed on a part of the body such as a fingertip. Similarly, a heart rate sensor measures a person's heart rate or pulse (generally in beats per minute), e.g., via a sensor placed on the chest or wrist.

Other useful proximal sensors are trajectory and pose sensors. For instance, an accelerometer can be used to detect the user's movement, speed and direction. A gyroscope sensor (often used in conjunction with an accelerometer) detects direction or orientation. A rate gyroscope similarly measures the rate of change of angle with time. A global positioning system or GPS provides location information.

Yet another type of sensor that is useful for the present techniques is an environmental sensor. For instance, a compass and/or a magnetometer (which measures the direction of magnetic fields) can be used to determine the physical position of the user. A barometer, air temperature sensors, wind speed sensors, etc. can be used to assess environmental conditions such as air pressure, temperature, wind velocity etc.

In step 104, a determination is made from the data collected in step 102 whether there is any potential for user impairment. For instance, if the user is suffering from a malady or medical condition such as dizziness due to high blood pressure or a heart condition, the user might be exhibiting non typical behavior. For example, if the data (from step 102) indicates that the user is presently at a location that is a health club or fitness center, yet the person is not moving and/or the data reflects a low heart rate/pulse, etc., then that might be considered an indicator of an impaired condition. By contrast, if the data reflects that the user is at home and it is nighttime, then one might assume that the user is asleep and thus has limited movement and a lower pulse. When the user behavior is not typical (which might reflect on the individuals alertness) it may be desirable to take further action to monitor, respond to, and/or alter the behavior.

From the above examples, it is apparent that the assessments made in step 104 (and elsewhere) may be based on the combination of data fused from different sensors. For instance, in the scenarios presented above, the physiological data collected from the heart rate, EDA, etc. sensors is fused with the pose, location, etc. sensors to make the determination of user impairment. Additional user and/or environmental data may also be fused with the sensor data. For instance, the user might provide data when initializing the system relating to the user's height, weight, age, medical conditions, etc. This information may also be garnered from the user's medical or other relevant records. Further, as highlighted above, data may also be collected from external sources, such as weather conditions from the national weather service, etc.

If it is determined in step 104 that (no) the collected data does not indicate any signs of user impairment, then no immediate action is taken. However, as shown in FIG. 1, the process continues to monitor the user's physical and surrounding environmental conditions in real-time. On the other hand, if it is determined in step 104 that (yes) the collected data does indicate some potential for user impairment, then in step 106 a corrective action is computed.

The appropriate corrective action, if any, can be based on a series of pre-determined scenarios. For instance, using the example above of a medical emergency, the corrective action might be to alert medical and/or emergency personnel, such as police, fire, or ambulance. Or, in the case of a user who is impaired from fatigue, a non-emergency medical condition that causes drowsiness, etc., the corrective action might be to schedule alternative transportation (such as by scheduling a taxi) and/or preventing the user from driving, such as disabling the user's vehicle.

It is notable that, as highlighted above, the corrective action might be to take no action at all. Take for instance, the situation where the data indicates that the user is experiencing drowsiness. However, the data suggests that the user is currently at his/her residence, and thus does not need to drive a car to get home. Then there might not be any corrective action needed.

In addition to monitoring and taking action based on a user's behavior, the present techniques also anticipate taking steps to modify the user's behavior, e.g., in situations where changing the user's behavior can reduce risks. Take for instance the situation where the user is exercising and the data collected in step 102 indicates that the user has an abnormally high heart rate, or low blood oxygenation. The present system can alert the user of this condition and attempt to regulate the user's behavior to reduce the potential risk. For example, if (via the sensor data) it is presumed that the user is running, a signal may be sent to the user's smartwatch to slow their pace, or to take a break. The smartwatch can monitor the user's pulse, blood oxygen levels, etc. and alert the user to resume exercise when they have reached normal levels.

Several different, non-limiting, techniques are anticipated herein for alerting the user. For instance, an audible alarm can alert the user to view text on his/her smartwatch display explaining the situation and suggested behavior modification. The alarm can be intensified if the user does not comply (e.g., the activity causing the condition is ongoing, and/or the detected symptoms don't change or are worsening). Similarly, voice commands can operate in the same general manner. Visual alerts can be in the form of text messages to the user on the smartwatch's display, or flashing different colors on the smartwatch's display. For example, under normal conditions the watch display might be blue. When an alert is generated, the color of the display can change (e.g., to red or flashing red). The frequency of the flashing can increase until it catches the user's attention. The display can return to a normal color/stop flashing when the data indicates that normal vitals have returned. Additionally, a vibrating alert feature may be used to get the user's attention. For instance, when the user's smartwatch vibrates, the user will know to read information off of the display.

In step 108, a determination is made as to whether any corrective action needs to be taken. Namely, as highlighted above, the corrective action might be to take no action at all. For instance, the data may indicate that the user is fatigued/drowsy, but is currently at his/her residence. There might not be any corrective action needed since the user does not need to drive a car to get home. Thus, if it is determined in step 108 that (no) no corrective action is needed, then no immediate action is taken. However, as shown in FIG. 1, the process continues to monitor the user's physical and surrounding environmental conditions in real-time.

On the other hand, if it is determined in step 108 that (yes) corrective action is needed, then in step 110 the appropriate action or actions (based on the determination made in step 106) are taken to respond to the impairment conditions and/or to modify the user's behavior. As provided above, responses to an impaired user condition can include, but are not limited to, alerting medical authorities when the person is experiencing a medical emergency, arranging alternative transportation for a user who is impaired and/or disabling the user's vehicle so as to prevent them from driving. Once the appropriate corrective action is taken, the process continues to monitor the user's physical and surrounding environmental conditions in real-time. See FIG. 1.

Figure 2:
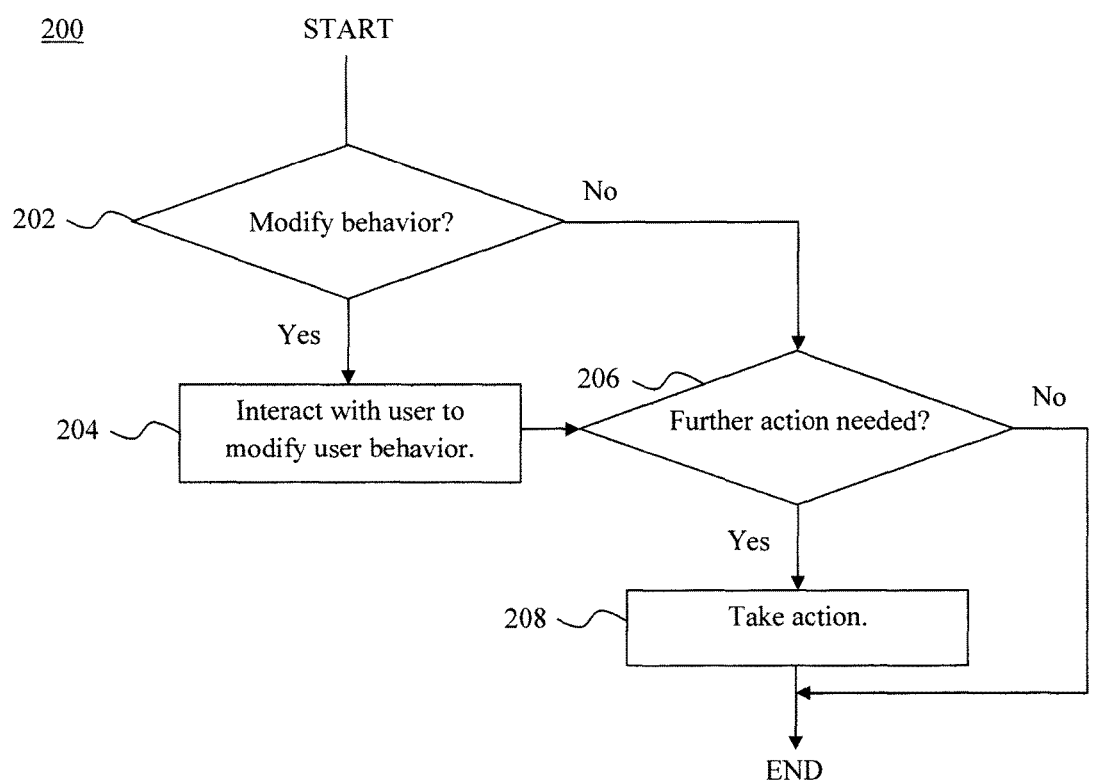
FIG. 2 is a diagram illustrating an exemplary methodology for taking corrective action to respond to impairment and/or to modify user behavior according to an embodiment of the present invention.

An exemplary embodiment for taking corrective action to respond to impairment and/or to modify user behavior is now described by way of reference to methodology 200 of FIG. 2. Methodology 200 represents one exemplary implementation of step 110 of FIG. 1. In this scenario it is assumed that an assessment has been made that an impairment condition might exist and an appropriate corrective action or actions has been determined. Thus following a determination in step 108 that (yes) corrected action should be taken, in step 202 a determination is made as to whether steps should be taken to modify the user's behavior. Take for instance the example provided above where the user's actions are causing the impairment condition, such as if the user is exercising beyond his/her capacity. In that case, there is the potential to modify the user's behavior to reduce risks of the user suffering a medical emergency, driving in an impaired state, etc. On the other hand, if the impairment condition is a medical emergency—for instance the user is unconscious or is suffering a heart attack—then there is no behavior to modify and immediate medical attention is necessary.

If it is determined in step 202 that (no) modifying the user's behavior modification is not warranted, then a determination is made in step 206 as to whether further action is needed. Step 206 is described in further detail below. As highlighted above, no behavior modification might be warranted, for example, in emergency situations where immediate medical attention is needed.

On the other hand, if it is determined in step 202 that (yes) the user's behavior can be modified, then in step 204 the mobile feedback controller worn by the user is used to interact with the user to attempt to modify the user's behavior. For instance, in the examples provided above, an alert (visual, audible, vibrating alert, etc. via the user's smartwatch) can be generated to alert the user of the condition and attempt to modify the user's behavior causing the condition. For example, the alert might tell the user to reduce his/her exercise regime when impairment conditions are detected—such as an abnormally high heart rate.

A determination is then made in step 206 as to whether further action is needed. For instance, in the case of a medical emergency one might need to alert the medical authorities, when a user is impaired it might be prudent to take steps to prevent them from driving, etc. If it is determined in step 206 that (no) further action is needed, then the process ends. As described in conjunction with the description of FIG. 1, above, continuous real-time monitoring is carried out to detect any changes in the user's condition.

On the other hand, if it is determined in step 206 that (yes) further action is needed, then the appropriate action is undertaken in step 208. For instance, in the case of a medical emergency, an alert may be sent to medical personnel describing the user and his/her condition and location. When a user is impaired (e.g., due to fatigue, drowsiness caused by a (non-emergency) medical condition, etc.) steps may be taken to prevent the user from driving. For instance, a request for alternative transportation may be sent, e.g., to a taxi service, the user's friends (via their smartwatches, mobile phones), etc. The user's car might also be disabled so that it cannot be driven. For instance, when the user approaches their car (which can be equipped with near field communication or NFC), this NFC program on their smartwatch tells the car not to open, or optionally to have the car open so person can sit inside, but not start.

Figure 3:
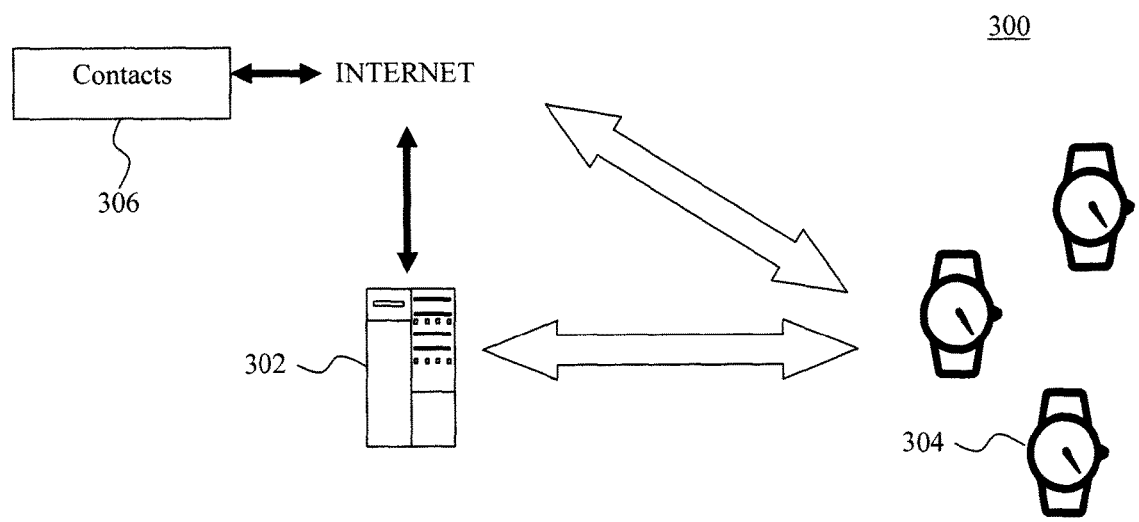
FIG. 3 is a diagram illustrating an exemplary system for user behavior monitoring and feedback control using smartwatches according to an embodiment of the present invention.

As described above, the present techniques can be implemented using smartwatch technology. Smartwatches can provide the platform of sensors needed to collect the vast types of data used for performing the present techniques. Smartwatches also provide the interactive capabilities to modify user behavior, when such action is warranted. Further, smartwatches can communicate with third party contacts, such as medical personnel, taxi service, etc., when such action is warranted. All of the above-described features may be embodied in the smartwatches themselves or, as shown in FIG. 3, one or more of the present capabilities may be performed by a central monitoring component 302. A suitable apparatus that may be employed as central monitoring component 302 is described, for example, in conjunction with the description of FIG. 4, below.

For instance, in one exemplary embodiment, a central monitoring component 302 may collect real-time data from one or more user's smartwatches 304. As per methodologies 100 and 200 described in conjunction with the description of FIGS. 1 and 2, above, the central monitoring component will analyze the data to determine whether an impairment condition exists and what, if any, corrective action should be taken. For instance, the central monitoring component 302 may alert third party contacts 306, e.g., via the internet, to request medical attention, or to arrange alternative transportation, etc. As provided above, relevant data may also be collected via the internet, such as weather data, user's medical records, etc. As shown in FIG. 3, the smartwatches 304 themselves can also have direct access to various contacts and other information via the internet.

A notable advantage of the present techniques is that the user's conditions, surrounding environment, etc. can be monitored passively—i.e., without needing proactive input from the user such as requiring the user to enter data, perform diagnostics such as taking their pulse, temperature, etc. Further, by leveraging the extensive capabilities of current mobile technology to gather vast categories of data in real-time and combining that data, the present techniques can be used to make significantly more accurate assessments than previously possible. For instance, being able to collect an array of physiological user data and combine that with environmental data, pose data, etc. results in a much more accurate diagnosis of the user's present conditions and risks. Also, by leveraging the interactive capabilities of such mobile technology, the present techniques can be employed to proactively modify user behavior, thereby reducing risks. This is something that simple passive monitoring cannot accomplish.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 4:
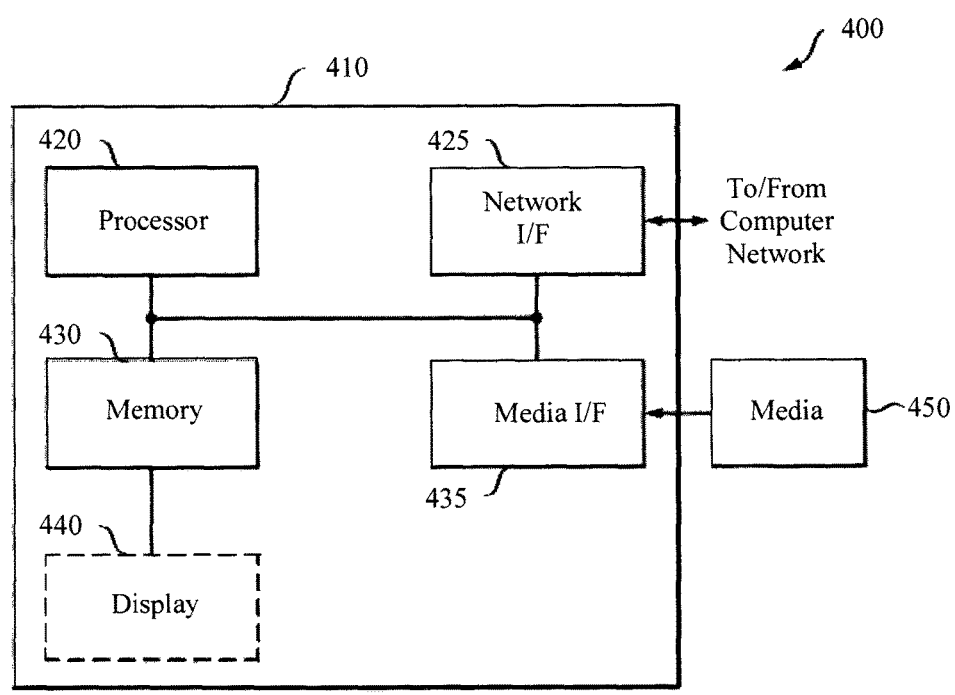
FIG. 4 is a diagram illustrating an exemplary apparatus for performing one or more of the methodologies presented herein according to an embodiment of the present invention.

Turning now to FIG. 4, a block diagram is shown of an apparatus 400 for implementing one or more of the methodologies presented herein. By way of example only, apparatus 400 can be configured to implement one or more of the steps of methodology 100 of FIG. 1, and/or one or more of the steps of methodology 200 of FIG. 2.

Apparatus 400 includes a computer system 410 and removable media 450. Computer system 410 includes a processor device 420, a network interface 425, a memory 430, a media interface 435 and an optional display 440.

Network interface 425 allows computer system 410 to connect to a network, while media interface 435 allows computer system 410 to interact with media, such as a hard drive or removable media 450.

Processor device 420 can be configured to implement the methods, steps, and functions disclosed herein. The memory 430 could be distributed or local and the processor device 420 could be distributed or singular. The memory 430 could be implemented as an electrical, magnetic or optical memory, or any combination of these or other types of storage devices. Moreover, the term "memory" should be construed broadly enough to encompass any information able to be read from, or written to, an address in the addressable space accessed by processor device 420. With this definition, information on a network, accessible through network interface 425, is still within memory 430 because the processor device 420 can retrieve the information from the network. It should be noted that each distributed processor that makes up processor device 420 generally contains its own addressable memory space. It should also be noted that some or all of computer system 410 can be incorporated into an application-specific or general-use integrated circuit.

Optional display 440 is any type of display suitable for interacting with a human user of apparatus 400. Generally, display 440 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for monitoring a user, the method comprising the steps of:
    collecting real-time data from the user relating to a physical condition and surrounding environment of the user, a current location of the user, and whether the user is at home, wherein the real-time data is collected via a mobile feedback controller worn by the user;
    determining the physical condition and a current location of the user by combining the real time data relating to the physical condition and surrounding environment of the user, and determining whether the current location of the user is a home of the user;
    determining whether the real-time data collected from the user indicates impairment by analyzing the real-time data relating to the physical condition and surrounding environment of the user, the current location of the user, and whether the user is at home;
    determining appropriate corrective actions to be taken if the real-time data collected from the user indicates impairment, otherwise continuing to collect data from the user in real-time;
    determining whether any action is needed; and
    undertaking the appropriate corrective actions if action is needed, otherwise continuing to collect data from the user in real-time, wherein the appropriate corrective action is based on a series of predetermined scenarios, and wherein the appropriate corrective actions comprise i) disabling a vehicle of the user so as to prevent the user from driving, and ii) sending a request for alternative transportation to at least one of a taxi service and friends of the user.

2. The method of claim 1, wherein the real-time data collected from the user comprises physiological data for the user selected from the group consisting of: skin electrical characteristics, blood oxygen levels, heart rate, pulse, and combinations thereof.

3. The method of claim 1, wherein the real-time data collected from the user comprises trajectory data for the user selected from the group consisting of: movement, speed, direction, orientation, location, and combinations thereof.

4. The method of claim 1, wherein the real-time data collected from the user comprises environmental data selected from the group consisting of: air pressure, temperature, wind velocity, and combinations thereof.

5. The method of claim 1, wherein the mobile feedback controller worn by the user comprises at least one sensor selected from the group consisting of: an electrodermal activity (EDA) sensor, a pulse oximeter sensor, a heart rate sensor, and combinations thereof.

6. The method of claim 1, wherein the mobile feedback controller worn by the user comprises at least one sensor selected from the group consisting of: a gyroscope sensor, a global positioning system (GPS) sensor, and combinations thereof.

7. The method of claim 1, wherein the mobile feedback controller worn by the user comprises at least one sensor selected from the group consisting of: a barometer, an air temperature sensor, a wind speed sensor, and combinations thereof.

8. The method of claim 1, wherein the mobile feedback controller worn by the user comprises a smartwatch.

9. The method of claim 1, further comprising the steps of:
    determining whether a behavior of the user is modifiable; and
    interacting with the user to modify the behavior of the user if the behavior of the user is modifiable, otherwise determining whether further action is needed.

10. The method of claim 9, wherein the step of interacting with the user to modify the behavior of the user comprises the steps of:
    generating an alert to the user on the mobile feedback controller worn by the user; and
    increasing an intensity of the alert to catch an attention of the user until the real-time data collected from the user no longer indicates impairment.

11. The method of claim 10, wherein the alert is selected from the group consisting of: an audible alarm, a visual alert, a vibrating alert, and combinations thereof.

12. The method of claim 11, wherein the audible alarm comprises voice commands.

13. The method of claim 11, wherein the visual alert comprises text on a display of the mobile feedback controller worn by the user.

14. The method of claim 1, wherein the appropriate corrective actions comprise alerting third party contacts.

15. The method of claim 14, wherein the third party contacts comprise medical personnel.

16. The method of claim 1, wherein the mobile feedback controller communicates with the vehicle by near field communication, and wherein disabling the vehicle comprises the step of:
    sending a communication from the mobile feedback controller to the vehicle, when the user approaches the vehicle, that prevents the vehicle from being opened by the user.

17. A computer program product for monitoring a user, the computer program product comprising a non-transitory computer readable storage medium having program instructions embodied therewith, the program instructions executable by a computer to cause the computer to:

collect real-time data from the user relating to a physical condition and surrounding environment of the user, a current location of the user, and whether the user is at home, wherein the real-time data is collected via a mobile feedback controller worn by the user;

determine whether the real-time data collected from the user indicates impairment by analyzing the real-time data relating to the physical condition and surrounding environment of the user, the current location of the user, and whether the user is at home;

determine appropriate corrective actions to be taken if the real-time data collected from the user indicates impairment, otherwise continue to collect data from the user in real-time;

determine whether any action is needed; and undertake the appropriate corrective actions if action is needed, otherwise continue to collect data from the user in real-time, wherein the appropriate corrective action is based on a series of predetermined scenarios, and wherein the appropriate corrective actions comprise i) disabling a vehicle of the user so as to prevent the user from driving, and ii) sending a request for alternative transportation to at least one of a taxi service and friends of the user.

18. The computer program product of claim 17, wherein the program instructions further cause the computer to:
determine whether a behavior of the user is modifiable; and
interact with the user to modify the behavior of the user if the behavior of the user is modifiable, otherwise determining whether further action is needed.

19. The computer program product of claim 18, wherein when interacting with the user to modify the behavior of the user the program instructions further cause the computer to:
generate an alert to the user on the mobile feedback controller worn by the user; and
increase an intensity of the alert to catch an attention of the user until the real-time data collected from the user no longer indicates impairment.

20. The computer program product of claim 19, wherein the alert is selected from the group consisting of: an audible alarm, a visual alert, a vibrating alert, and combinations thereof.

* * * * *